US008367128B2

(12) United States Patent (10) Patent No.: US 8,367,128 B2
Girault et al. (45) Date of Patent: Feb. 5, 2013

(54) METHOD FOR MAKING A FOOD OR BIOTECHNOLOGICAL PRODUCT USING REDOX POTENTIAL REGULATION

(75) Inventors: Christel Girault, Voisins le Bretonneux (FR); Dominique Ibarra, Gif-sur-Yvette (FR)

(73) Assignee: L'Air Liquide Societe Anonyme pour l'Etude et l'Exploitation des Procedes Georges Claude, Paris (FR)

( * ) Notice: Subject to any disclaimer, the term of this patent is extended or adjusted under 35 U.S.C. 154(b) by 784 days.

(21) Appl. No.: 12/088,633

(22) PCT Filed: Aug. 8, 2006

(86) PCT No.: PCT/FR2006/050792
§ 371 (c)(1),
(2), (4) Date: Mar. 28, 2008

(87) PCT Pub. No.: WO2007/036653
PCT Pub. Date: Apr. 5, 2007

(65) Prior Publication Data
US 2010/0151077 A1 Jun. 17, 2010

(51) Int. Cl.
*A23C 9/12* (2006.01)
(52) U.S. Cl. .............. 426/34; 426/42; 426/43; 426/580; 426/583
(58) Field of Classification Search .................... 426/34, 426/42, 43, 580, 583
See application file for complete search history.

(56) References Cited

U.S. PATENT DOCUMENTS

| 3,201,328 A * | 8/1965 | Williams .................... 435/294.1 |
| 5,453,286 A | 9/1995 | Castberg et al. |
| 7,078,201 B2 * | 7/2006 | Burmaster .................... 435/161 |
| 2003/0162272 A1 | 8/2003 | Cachon et al. |

FOREIGN PATENT DOCUMENTS

| FR | 2 610 795 | 8/1988 |
| FR | 2 811 331 | 1/2002 |
| FR | 2848122 | 6/2004 |
| GB | 1 057 754 | 2/1967 |
| RU | 2 220 580 | 1/2004 |
| WO | WO 98/27824 | 7/1998 |
| WO | WO 02/02748 | 1/2002 |

OTHER PUBLICATIONS

Chen et al., Anaerobic yeast fermentation for the production of ethanol in a versatile lab fermentor, Dec. 2008, Nature Methods, an4-an5.*
R & D Laboratory, New Brunswick Scientific, Using redox measurements to control an anaerobic yeast fermentaion, 2008, BioTechniques, vol. 45, No. 6, pp. 670-671.*
Beresford, et al., "Recent Advances in Cheese Microbiology," International Dairy Journal, 11, 2001, pp. 259-274.
PCT/FR2006/050792 International Search Report mailed Jan. 2, 2007.
Urbach, et al., "Contribution of Acid Bacteria to Flavour Compound Formation in Dairy Products," International Dairy Journal, 5, 1995, pp. 877-903.
Henriksen, et al., published in Letters in Applied Microbiology in 2000, vol. 30, pp. 415-418.
Dave, et al., "Effect of Cysteine on the Viability of Yoghurt and Probiotic Bacteria in Yoghurts made with Commercial Starter Cultures," International Dairy Journal, published 1997, pp. 31-41.
Green, et al., "Development of Texture and Flavour in Cheese and other Fermented Products," Journal of Dairy Research, No. 49, published 1982, pp. 737-748.
Kristoffersen, et al., "Consumer Packaged Cheese II. Chemical Changes," Journal of Dairy Science, No. 47, published 1964, pp. 743, 747.
Kristoffersen, T., "Development of Flavor in Cheese," Milchwissenschfat, No. 40, published 1985, pp. 197-199.
Kwong, et al., "Effect of Reducing Agents in an Aerobic Amino Acid Fermentation," Biotechnology & Bioengineering, No. 40, published 1992, pp. 851-857.
Law, et al., "The Contribution of Starter Streptococci to Flavour Development in Cheddar Cheese," Journal of Dairy Research, No. 43, published 1976, pp. 301-311.
PCT/FR2006/050275 International Search Report mailed Sep. 26, 2006.

* cited by examiner

*Primary Examiner* — Leslie Wong
(74) *Attorney, Agent, or Firm* — Christopher J. Cronin

(57) ABSTRACT

The invention concerns a method for producing a food or biotechnological product including one or more steps, said one or more steps being implemented in a medium, said one or more steps implemented in a medium being a fermentation step, which consists in: during at least one of the steps of the method in controlling the redox potential of the medium of the step concerned. Said method is characterized in that it consists in carrying out the process as follows: regulating at a predetermined setpoint level the redox potential of the medium of the step whereof the redox potential is controlled by controlled additions of a process gas into the medium concerned; and proceeding to the step following the step concerned in the process when said setpoint value is reached so as to carry out at least one of said steps of the process in reducing condition and at least one of said steps of the process in oxidizing condition.

19 Claims, 1 Drawing Sheet

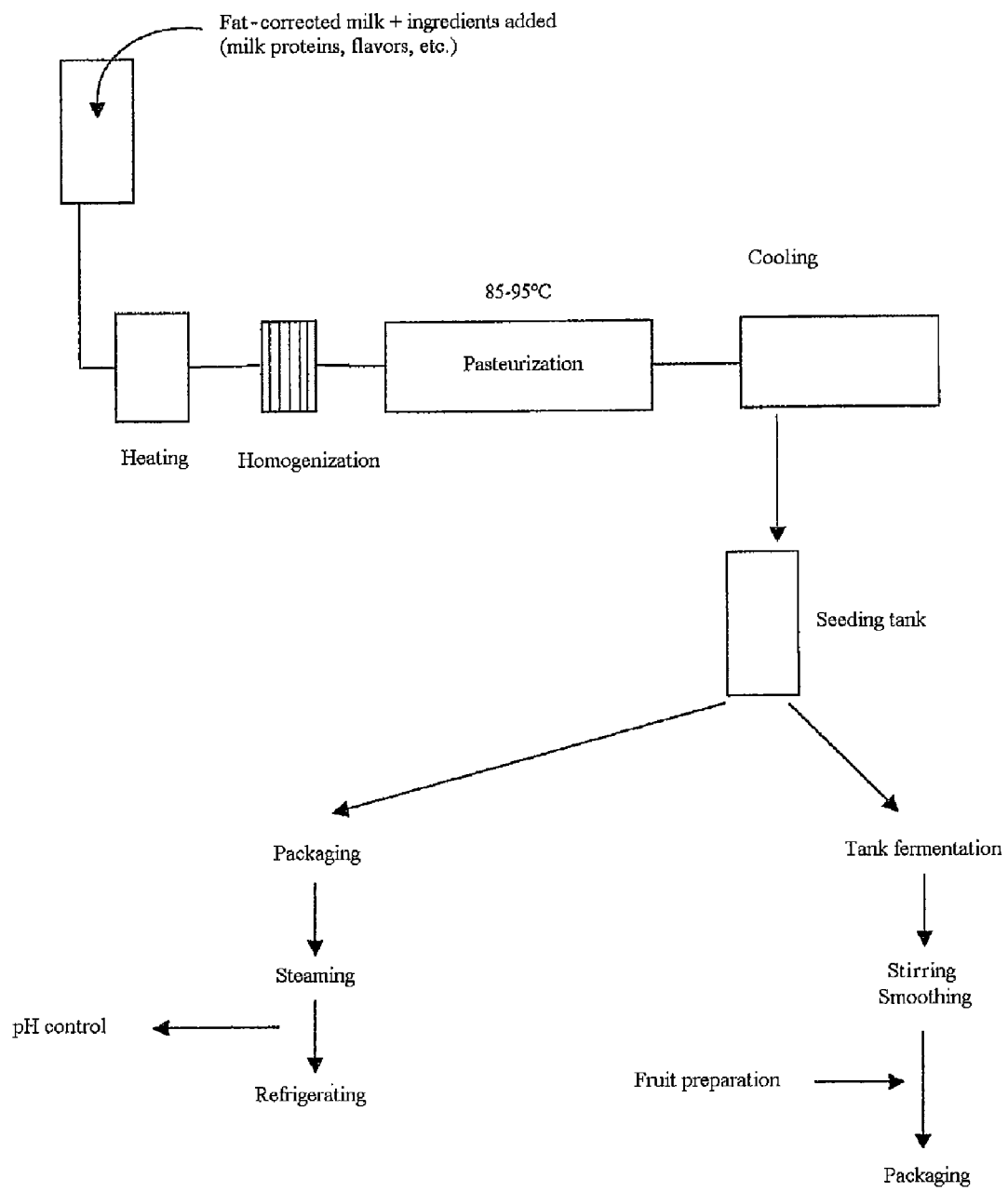

METHOD FOR MAKING A FOOD OR BIOTECHNOLOGICAL PRODUCT USING REDOX POTENTIAL REGULATION

This application is a 371 of International PCT Application PCT/FR2006/050792, filed Aug. 8, 2006.

BACKGROUND

The present invention relates to the field of processes for producing food and biotechnological products by implementing one or more fermentation steps.

The methods envisioned are very varied and can be divided up into two major groups:
- methods for making fermented food products such as fermented milk products (yoghurts, fromage blanc, etc.), fermented drinks (beers, wine, etc.),
- methods for making a biomass (lactic ferments, yeasts, etc.) and metabolites (food ingredients, molecules of interest such as enzymes, amino acids, medicaments, ethanol, etc.).

The invention endeavors to propose novel operating conditions that make it possible, depending on the case in question, to improve in particular the properties of the products thus produced, and in particular their microbiological properties, sensory properties, physicochemical properties, etc., or else the yields, purities, etc.

As will be seen below in greater detail, the present invention proposes a novel method for carrying out such processes by controlling and regulating the redox potential of the medium under consideration at a given redox potential level (redox level defined in each case so as to have an optimum desired effect), at one or more key points of the method, by controlled additions of one or more suitable gases or gas mixtures.

Redox potential measurements can be obtained in a medium using any available means, such as, for example, redox probes which make it possible to carry out direct and continuous measurements in liquid or semi-liquid media, or else to carry them out indirectly through measurements of dissolved gas content, for example of dissolved hydrogen in the medium.

The monitoring and the regulating of the redox potential at certain key steps of the process make it possible, for example, to carry out steps or phases of the process under stable reducing conditions or to alternate, during the process, between steps under reducing conditions and steps under oxidizing conditions.

A condition is considered to be oxidizing or reducing relative to the redox potential of the medium before the adjustment with the gases. Thus, a condition will be termed reducing when the oxidoreduction potential is less than the initial value before its adjustment and its regulation (irrespective of whether or not the potential reached is negative). Conversely, a condition will be termed oxidizing when the oxidoreduction potential is greater than the initial value before its adjustment and its regulation (irrespective of whether or not the potential reached is positive).

It will be recalled that oxidoreductions are essential steps in cell anabolism and catabolism reactions, for which the direction of the exchanges is determined by the oxidoreduction potential (hereinafter Eh). The Eh is a fermentation state parameter; variation thereof modifies the physicochemical environment of microorganisms. The metabolic activities and the physiology of microorganisms are determined by the intracellular pH ($pH_{in}$) which will condition the activity of the enzymes and the accessibility of certain substrates and cofactors in the metabolic reactions. The $pH_{in}$ depends on the extracellular pH ($pH_{ex}$) and on the ability of the microorganism to maintain a certain cellular homeostasis. The difference between the $pH_{in}$ and the $pH_{ex}$ will also modify the value of the proton motive force $\Delta\mu H^+$, which is in particular involved in the exchanges of the microbial cell with the exterior. The Eh and $pH_{in}$ parameters are intimately linked; thus, the energy found in high-potential compounds, such as adenosine triphosphate (ATP), and gained by substrate catabolism may be used by the cell in order to maintain its $pH_{in}$ (and therefore its $\Delta pH$) by virtue of membrane ATPases.

According to Urbach et al., in 1995 ("Contribution of lactic acid bacteria to flavour compound formation in dairy products", International Dairy Journal, 5: 877-903), lactic acid bacteria are widely involved in the production of the flavor compounds of fermented dairy products; they convert lactose to lactic acid; this results in the production of diacetyl and of acetaldehyde, which are the principle flavor compounds of fermented milks and of fromage frais. The Eh is an environmental parameter which will be able to condition the metabolic activities of microorganisms and in particular their ability to synthesize flavor molecules. In particular, it has been shown, for emmental and cheddar, that good-quality cheeses have a low oxidoreduction potential.

The Eh is a physicochemical parameter which, by virtue of its nature, acts on all media, provided that the latter contain at least one molecule which can pass from an oxidized state to a reduced state and vice versa. For this reason, its effect can be seen on all cellular functions. Its action has been shown on various types of bacterial strains; by way of illustration:
- the addition of chemical reducing agents to culture media has made it possible to significantly modify growth and metabolic fluxes in *Corynebacterium glutamicum, Clostridium acetobutylicum, Sporidiobolus ruinenii* and *Escherichia coli;*
- a reducing Eh fixed by gases has made it possible to modify the metabolic fluxes in *Saccharomyces cerevisiae* with an increase in the glycerol/ethanol ratio and the accumulation of storage sugars with an increase in yeast survival during conservation.

In the industrial environment, the Eh is already indirectly taken into account through oxygen, the inhibitory effect of which on lactic acid bacteria has been well identified. This effect is due to their inability to synthesize cytochromes and enzymes containing a heme nucleus.

It is, moreover, known that it is also possible, by acting on the Eh, to modify the survival of probiotic ferments, metabolic fluxes, and the production and/or the stability of flavor molecules. All these results were obtained following modification of the Eh by the microorganisms themselves, by oxidoreductive molecules, or by thermal treatment.

In the field of the use of gas mixtures in lactic acid bacteria fermentation media, mention may also be made of the studies by Henriksen et al., published in Letters in Applied Microbiology in 2000 (Vol. 30 p. 415-418), which focus on the growth of lactic acid bacteria, and showed that, when the cultures were swept with nitrogen, growth was greatly slowed, whereas the addition of minute amounts of $CO_2$ in this case caused the growth to begin again in exponential form.

The present invention therefore relates to a process for producing a food or biotechnological product, implementing one or more steps, wherein one or more of the steps uses a medium, one or more of the steps that uses a medium being a fermentation step, said process consisting, during at least one of the steps thereof, in controlling the redox potential of the medium of the step in question, and being characterized in that it is conducted in the following way:

regulating at a predetermined setpoint level the redox potential of the medium of the step of which the redox potential is controlled with controlled additions of a process gas to the medium in question, and proceeding to the step that follows said step in question in the process when said setpoint value is reached, so as to carry out at least one of said steps of the process under reducing conditions and at least one of said steps of the process under oxidizing conditions.

In the subsequent text, reference will be made without distinction to steps or phases constituting the process, or alternatively to phases constituting a step of the process.

The process according to the invention may, moreover, adopt one or more of the following technical characteristics:

the process is a process for producing a fermented milk product, and the regulating of the redox potential is carried out in several of the steps so as to sequence the oxidation and reduction phases in the following way:

the redox potential is regulated so as to set up reducing conditions at one or more points of the process located upstream of the pasteurization phase;

the redox potential is regulated so as to set up oxidizing conditions at one or more points of the process located downstream of the pasteurization;

the process is a process for producing a fermented milk product, and the regulating of the redox potential is carried out in several of the steps so as to sequence the oxidation and reduction phases in the following way:

the redox potential is regulated so as to set up oxidizing conditions at one or more points of the process located upstream of the pasteurization phase;

the redox potential is regulated so as to set up reducing conditions at one or more points of the process located downstream of the pasteurization;

the fermented milk product is a yoghurt;

said conducting of the process is done in such a way that, for at least one of said fermentation steps, controlled addition of a process gas make it possible to alternate between phases of the fermentation in question under reducing conditions and phases of the fermentation in question under oxidizing conditions;

the process is a process for producing beer, and said conducting of the process allows the regulating of the redox potential during the fermentation to take place in two steps: in a first step, the fermentation takes place under regulated oxidizing conditions and in the presence of oxygen, so as to promote the growth of the yeast and a good physiological condition thereof, and in a second step, the redox potential is reduced to an optimal value so as to make it possible to improve the fermentation parameters, and also the sensory criteria;

the process is a fermentation process in a fermenter, aimed at the production of biomass and/or of metabolites, and said conducting of the process makes it possible to regulate the redox potential of the medium at various successive values according to the various fermentation phases, so as to carry out a first phase under oxidizing conditions in order to promote the growth of the microbial strain through oxidizing conditions and, after a maximum biomass content has been obtained, to switch the fermenter to reducing conditions in order to initiate or intensify the production of one or more desired metabolites;

the process is a fermentation process in a fermenter, aimed at the production of biomass and/or of metabolites, and said conducting of the process makes it possible to regulate the redox potential of the medium at various successive values according to the various fermentation phases, so as to carry out a first phase rendered slightly reducing, which is favorable to the growth of certain microorganisms and therefore to the production of a large biomass, followed by a more reducing phase which will make it possible to promote the production of desired flavor compounds;

the process is a fermentation process in a fermenter, aimed at the production of biomass and/or of metabolites, and said conducting of the process makes it possible to modify and regulate the redox potential of the medium at a different value at the end of fermentation in order to adapt the metabolism or the physiology of the microorganisms so as to prepare them for a subsequent step;

the process is a fermentation process in a fermenter, aimed at the production of biomass and/or of metabolites, and said conducting of the process makes it possible to change the redox potential level after the production of a desired metabolite so as to promote the excretion of the metabolite in question into the recovery medium;

the process is a fermentation process in a fermenter, aimed at the production of biomass and/or of metabolites, and said conducting of the process makes it possible to change the redox potential level after the production of a precursor of a molecule of interest so as to promote a chemical reaction for obtaining the desired molecule of interest;

the process is a fermentation process in a fermenter, aimed at the production of biomass and/or of metabolites, and in that, subsequent to the fermentation, the following are carried out:

centrifugation and/or filtration and/or ultrafiltration steps aimed at recovering the biomass produced, or purification steps on the fermentation medium in order to separate and concentrate metabolites, and said conducting of the process makes it possible to change the redox potential level after the separation of the medium containing the molecule of interest from the biomass (microbial cells) so as to promote the selective separation of the molecule of interest from the other compounds of the medium by promoting, for example, the binding to a resin either in the reduced form or in the oxidized form of the molecule of interest and elution thereof with a suitable solution.

It is therefore proposed to control the redox potential at key places in the process using any available means such as, for example, redox probes. This control makes it possible to adjust the redox potential and to control the addition of gas to the medium, while at the same time accurately determining the moment when it is possible to stop the redox modification process.

It is possible to envision a system for automatically regulating the redox potential of the medium, since it is known, for example, that certain microorganisms, by virtue of their activity, modify the redox potential of a medium. It is thus possible to keep a stable redox potential for a given period of a fermentation.

It may also be possible, according to the process in question, to alternate between phases of reducing conditions and oxidizing conditions so as to promote, at defined moments in the process, the setting up of biochemical and/or biological reactions which, by virtue of the sequencing, make it possible to obtain a product with defined characteristics. Thus, by way of illustration, it may be advantageous to conduct a fermentation with a first phase rendered slightly reducing by the addition of nitrogen (driving off part of the dissolved oxygen) which is favorable to the growth of certain microorganisms and therefore to the production of a large biomass, followed by a more reducing phase (for example using a mixture containing hydrogen) which will make it possible, for example, to promote the production of desired flavor compounds such as, for example, the acetaldehyde produced by lactic acid bacteria.

As will have been understood from reading the above, the process gas would have to be chosen according to the process in question, the step in question, and the redox conditions that it is desired to reach, and it will therefore be possible to envision using a neutral gas such as nitrogen, argon, helium or carbon dioxide, and also an oxidizing gas such as oxygen or air, or alternatively a reducing gas such as hydrogen, or even a mixture of such gases.

BRIEF DESCRIPTION OF THE DRAWINGS

Other characteristics and advantages will emerge from the following description, given only by way of example and produced in particular with reference to the FIGURE which illustrates an example of application of the invention in the case of an installation for producing yoghurts or other fermented milk products.

The following elements and steps are recognized in FIG. 1:
preparation of the milk, which generally comprises the addition of components such as fats or proteins or else flavors so as to fix the composition thereof;
a heating step;
a pasteurization step (heat treatment);
homogenization (which can take place before or after the pasteurization);
cooling to the temperature at which the seeding will take place;
seeding with the desired strains;
according to the type of yoghurt or fermented milk product in question: tank fermentation followed by smoothing before packaging (for example: "stirred" yoghurts), or else prior dispensing of the seeded mixture into pots where the fermentation will take place (for example: "set" or "steamed" yoghurts);
cooling of the products before storage thereof.

It is accordingly possible to envision carrying out a regulation of the redox potential at the following points of the chain:
i) in the starting milk before fat correction,
j) in the milk mixture resulting from the addition of the additional ingredients to the milk;
k) before or after the step of homogenizing said milk mixture;
l) before or after the step of pasteurizing the milk mixture;
m) before or after the step of seeding the milk mixture with one or more strains of lactic acid bacteria;
n) before the packaging of the product in its final packaging.

In accordance with the invention, in this case of the production of yoghurts or fermented milk products, it is possible to envision sequencing the oxidation and reduction phases. In fact, without being at any time bound by the explanation which follows, it may be considered that the reducing values will be able to favorably adjust the conformation of the proteins, in particular the serum proteins, rich in sulfur molecules. The redox potential makes it possible to adjust the state of these molecules which are in the form of thiol groups or in the form of disulfide bridges, and play an essential role in the formation of the protein network after denaturation of the proteins during the pasteurization step. The use of reducing conditions upstream of the pasteurization phase will therefore make it possible to couple this effect with the effect of the heat on the proteins, resulting in the production of protein gels having a stable structure that will be favorable in particular to a limitation of the syneresis phenomena in yoghurts. Downstream of the pasteurization, it will then be advantageous to re-establish less reducing redox values (or redox values equal to the normal values of milk) which will allow the seeded bacteria to develop normally without influencing their metabolism and therefore without any organoleptic consequence.

It may also be advantageous to adjust a target value of the redox potential during the fermentation in order to intentionally influence the metabolism of the lactic ferments, and thus, for example, to direct the production of flavors toward the desired compounds.

By switching so as to finish with the redox potential of the finished product at a more reducing value than that of the fermentation, it will be possible to microbiologically stabilize the yoghurt and thus to more effectively preserve it against the possible development of certain yeasts or molds.

In the above text, examples of the production of yoghurts have more particularly been developed, but mention may also be made of the case of the production of fermented drinks such as beer, and also the case of the production of products in fermenters. This will be done below.

The case of beer production will therefore now be discussed.

Shown below will be the fact that, in the case of beer production, it is advantageous to conduct the process in such a way that the regulating of the redox potential during the fermentation takes place in two steps, in two phases. In a first step, the fermentation advantageously takes place under regulated oxidizing conditions and in the presence of oxygen, so as to promote the growth of the yeast and a good physiological condition thereof. In a second step, the redox potential is reduced to an optimal value so as to make it possible to improve the fermentation parameters and also the sensory criteria (flavors, foam retention).

It should be recalled that the brewing process typically comprises two fermentation steps:
the main fermentation: after aeration of the wort, the latter is seeded with a yeast of the *Saccharomyces* genus, which will, through fermentation, convert the fermentable sugars to alcohol and to carbon dioxide.
the secondary fermentation or "standing": this step is carried out subsequent to the previous step by reducing the temperature of the medium to a temperature close to 0° C. for a period which varies from a few days to a few weeks. The young beer will become saturated with carbon dioxide, which will greatly contribute to its foaming character. It is also during this maturing phase that the beer clarifies and that its flavor matures.

The examples which follow will show that it is advantageous to ferment the wort under oxidizing conditions at selected moments and under reducing conditions at selected moments.

EXAMPLE(S)

Example 1

Six "Kirin"-type wort fermentation tests were carried out using a malt extract (this test is well known to those skilled in the art; it is a predictive test that is autonomous, i.e. not part of the overall beer-producing process): 2 control worts (average redox potential: 400 mV), 2 worts whose redox potential was reduced by initial bubbling with nitrogen (average redox potential: 140 mV), and 2 worts whose redox potential was reduced by initial bubbling with a nitrogen/hydrogen (96/4)

mixture (average redox potential: −415 mV). The worts were seeded with an active dry yeast at 11×10$^6$ viable cells per ml. The objective was to determine the influence of the redox potential on the fermentative performance of the yeast, for 8 days at 8° C.

The following parameters were monitored:
the decrease in the fermentable extract for 8 days,
the change in turbidity of the fermentation wort (growth of the yeast) by measuring the optical density of the wort at 800 nm for 8 days,
the fermentation parameters: apparent extract (fermentable extract plus nonfermentable extract) of the wort at the end of the test, apparent attenuation (percentage of fermentable extract used by the yeast relative to the total extract of the wort), degree of attenuation (proportion of the fermentable extract used by the yeast relative to the total fermentable extract).

The results (reported in table 1) show that decreasing the redox potential of the wort leads to an improvement in the fermentation parameters: decrease in the apparent extract, increase of the degree of attenuation and of the apparent attenuation, and increase of the optical density. These results reflect a greater use of fermentable sugars and a greater growth of the yeast under more reducing conditions.

TABLE 1

Average values of the results of the fermentation tests

|  | Control | N$_2$ condition | N$_2$/H$_2$ condition |
|---|---|---|---|
| Apparent extract at the 8$^{th}$ day (degrees Plato) | 3.27 | 3.04 | 2.62 |
| Apparent attenuation at the 8$^{th}$ day (%) | 70.3 | 72.4 | 76.0 |
| Degree of attenuation (%) | 90.8 | 93.4 | 97.8 |
| Optical density at the 8$^{th}$ day (at 800 nm) | 1.22 | 1.5 | 1.52 |

Example 2

Six 30-liter microbrewing (microproduction of beer) tests were carried out in the following way: 2 aerated control worts (average redox potential: 291 mV), 2 worts whose redox potential was reduced by initial bubbling with nitrogen (average redox potential: 216 mV) and 2 worts whose redox potential was reduced by initial bubbling with a nitrogen/hydrogen (96/4) mixture (average redox potential: −290 mV). The beers thus obtained were analyzed. In summary, the redox potential of the wort before heating is controlled, the rest of the production chain is conventional.

The results given in table 2 show that modifying the redox potential makes it possible to improve the foam retention. In fact, the lower the redox potential, the longer the foam retention.

Moreover, the sensory analysis (carried out in the form of triangular tests) shows significant differences (at the threshold of 5%) between the control beer and that obtained after reduction of the redox potential with the N$_2$/H$_2$ mixture. The descriptors cited (oxidized, high acidity) with respect to the control beer denote a certain oxidation state of the beer, more pronounced than the beer obtained with the N$_2$/H$_2$ mixture.

On the other hand, a slight tendency toward an increased SO$_2$ content of the beers derived from the worts with reduction of the redox potential with N$_2$ or N$_2$/H$_2$ is noted. The SO$_2$ content generally increases according to the poor physiological condition of the yeasts. The increase observed here is certainly explained by the lack of aeration of the yeast.

The reducing conditions therefore improve the sensory quality of the beer, without however improving the fermentation parameters in the manner described in Example 1.

TABLE 2

Results of beer analysis (average values of the 2 repeats for the foam retention, and values of the 2 repeats for the SO$_2$ content).

|  | Control | | N$_2$ condition | | N$_2$/H$_2$ condition | |
|---|---|---|---|---|---|---|
| Retention of foam (s) (NIBEM method) | 266 | | 278 | | 293 | |
| SO$_2$ (mg/l) | <1 | <1 | <1 | 3.8 | <1 | 2.6 |

It has thus clearly been shown by the above that, in the case of beer production, it is advantageous to carry out the procedure such that the regulating of the redox potential during the fermentation takes place in two steps. In a first step, the fermentation takes place under regulated oxidizing conditions and in the presence of oxygen, so as to promote growth of the yeast and a good physiological condition thereof. In a second step, the redox potential is reduced to an optimal value so as to make it possible to improve the fermentation parameters and also the sensory criteria (flavors, foam retention).

The case of fermenter productions will now be mentioned below.

In general, fermenter productions meet two needs, separately or simultaneously: the production of biomass and/or the production of molecules of interest. Several objectives may be sought:
the production of biomass,
the production of biomass coupled to that of molecules of interest (primary metabolites),
the production of molecules of interest other than those produced at the same time as the biomass, i.e. secondary metabolites,
the production of biomass and then of molecules of interest carried out in sequence.

Various types of culture exist:
batch culture, for which the culture medium is introduced in a single step at the beginning, without any introduction or extraction of medium during the fermentation,
fed-batch culture, used for example for the production of biomass sensitive to substrate inhibition, and for which the continuous or periodic introduction of nutrients is coupled to the growth, without any continuous removal of medium being carried out,
continuous culture, for which the microorganisms are maintained in the exponential growth phase through the continuous introduction of a new medium which balances out the continuous removal of medium containing the cells in suspension.

These fermentations, whether they are aerobic or anaerobic, take place in a fermenter or bioreactor, with or without stirring, in a medium whose composition is defined so as to direct the fermentation toward the desired production. Similarly, the fermentation parameters, such as pH, temperature, dissolved oxygen pressure, stirring speed, etc., are in general regulated at predetermined optimum values so as to maximize the desired production.

It is known that the redox potential may be continually changing during a fermentation for one or more of the following reasons:
the growth of the microorganisms,
the production of oxidizing or reducing molecules by the microorganisms,
the introduction of new culture medium in the case of fed-batch and continuous cultures.

The present invention therefore proposes to continually control the redox potential and to regulate it at its optimum value by using controlled additions of gas.

This optimum value is predetermined experimentally so as to optimize the desired reaction at a given moment of the fermentation.

Advantageously, it will be possible to associate or not associate with this regulation an adjustment of the redox potential of the new culture medium introduced in the case of fed-batch and continuous cultures.

According to one of the aspects of the invention, the redox potential of the medium is regulated at various successive values according to the various periods of the fermentation, in such a way as to control said fermentation so as to direct it toward one desired reaction or another.

The fermentation may thus be regulated under reducing conditions in a first step and then regulated under more oxidizing conditions in a second step, and vice versa:

- it is possible, for example, to choose to promote the growth of the microbial strain by oxidizing conditions and, after a maximum biomass content has been obtained, to switch the fermenter to more reducing conditions in order to initiate or intensify the production of one or more desired metabolites. It is known, for example, that *Saccharomyces* develops better under oxidizing conditions and produces more glycerol under reducing conditions. Similarly, it is known that cultures of *Corynebacterium glutamicum* produce more amino acids under reducing conditions or that *Sporidiobolus* produces more flavor compounds in a reducing medium;
- it is also possible, by regulating the redox potential of the medium at a different value at the end of fermentation, to adapt the metabolism or the physiology of the microorganisms in order to prepare them for a subsequent step. It may thus be advantageous, for example, to produce *Saccharomyces cerevisiae* in the presence of oxygen and to switch the medium for production of this yeast to an optimum reducing level in order to adapt it to its future use, for instance breadmaking.

The fermentation can thus be controlled at 2 or 3 successive redox values, or even more as required. Thus, it is possible to envision changing the level of regulation again after the production of the desired metabolite (for example, the production of a parietal enzyme) before harvesting or separation thereof from the culture medium and therefore at the end of fermentation, so as to promote the excretion of the metabolite under consideration into the recovery medium. This change in redox potential may also take place after the production of a precursor for the molecule of interest, which, under reducing conditions, will undergo a chemical reaction making it possible to obtain the molecule of interest in question.

It is known, moreover, that, after the fermentation per se, several processes may be applied. Centrifugation, filtration or ultrafiltration steps make it possible to recover the biomass produced. Purification steps may be carried out on the fermentation medium in order to separate and concentrate metabolites: centrifugation, filtration, chromatography, precipitation by addition of salts or solvent, etc.

The invention therefore proposes to regulate the redox in order to promote the separation of these molecules of interest. For example, the production and/or the excretion into the culture medium takes place under oxidizing (or reducing) conditions, and the conditions are switched to reducing (or oxidizing) conditions in order to carry out the separation step. Thus, for example, a molecule may be retained in a chromatography column by binding to a resin under oxidizing conditions and then be subsequently released in a reducing eluting solution.

While, in the processes targeted by the present invention, comprising one or more fermentation steps, the seeding of the medium can be carried out directly, it is also possible to envision it being carried out indirectly through the fact that one or more successive precultures are carried out beforehand in order to constitute the inoculum which will be used to seed the fermentation medium, and it is then also possible to envision, according to the present invention, carrying out a control and a regulation of the redox potential of the preculture with controlled additions of a process gas to the preculture medium under consideration.

It will be understood that many additional changes in the details, materials, steps and arrangement of parts, which have been herein described in order to explain the nature of the invention, may be made by those skilled in the art within the principle and scope of the invention as expressed in the appended claims. Thus, the present invention is not intended to be limited to the specific embodiments in the examples given above.

What is claimed is:

1. A method of making a fermented milk product, comprising the steps of:
    seeding a composition comprising milk with one or more strains of lactic acid bacteria, wherein before seeding:
        the composition is optionally provided with additional fat, protein or flavoring;
        the composition is optionally homogenized;
        the composition is optionally pasteurized;
    allowing the seeded composition to ferment;
    packaging the seeded composition or fermented composition;
    controlling a redox potential of a first medium to a desired first setpoint through addition of a process gas to the medium, the first medium being selected from the group consisting of:
        the unseeded composition before or after the optional addition of fat, protein, or flavoring;
        the unseeded composition before or after the optional homogenization;
        the unseeded composition before or after the optional pasteurization;
        the unseeded composition before seeding;
        the seeded composition before packaging; and
        the fermented composition before packaging; and
    discontinuing said process gas addition to the first medium when said desired first setpoint is reached, wherein:
        the desired first setpoint is higher or lower than a redox potential of the first medium before said process gas addition; and
        the process gas comprises a neutral gas and either an oxidizing gas or a reducing gas, the neutral gas selected from the group consisting of nitrogen, argon, helium, carbon dioxide, and mixtures thereof, the oxidizing gas being selected from the group consisting of oxygen, air, and mixtures thereof, the reducing gas being hydrogen.

2. The method of claim 1, wherein the composition is provided with additional fat, protein or flavoring before seeding.

3. The method of claim 1, wherein the composition is homogenized and cooled before seeding.

4. The method of claim 1, wherein the composition is pasteurized before seeding.

5. The method of claim 1, wherein said step of allowing the seeded composition to ferment is performed before said step of packaging.

6. The method of claim 1, wherein said step of allowing the seeded composition to ferment is performed after said step of packaging.

7. The method of claim 2, wherein said medium is the unseeded composition before the addition of fat, protein, or flavoring.

8. The method of claim 2, wherein said medium is the unseeded composition after the addition of fat, protein, or flavoring.

9. The method of claim 3, wherein said medium is the unseeded composition before homogenization.

10. The method of claim 3, wherein said medium is the unseeded composition after homogenization.

11. The method of claim 4, wherein said medium is the unseeded composition before pasteurization.

12. The method of claim 4, wherein said medium is the unseeded composition after pasteurization.

13. The method of claim 1, wherein said medium is the unseeded composition.

14. The method of claim 1, wherein said medium is the seeded composition before packaging.

15. The method of claim 1, wherein said medium is the fermented composition before packaging.

16. The method of claim 1, wherein said fermented milk product is yoghurt.

17. The method of claim 1, further comprising the steps of:
controlling a redox potential of a second medium to a desired second setpoint through addition of a process gas to the second medium, the second medium being different than the first medium, the second medium being selected from the group consisting of:
the unseeded composition before or after the optional addition of fat, protein, or flavoring;
the unseeded composition before or after the optional homogenization;
the unseeded composition before or after the optional pasteurization;
the unseeded composition before seeding;
the seeded composition before packaging; and
the fermented composition before packaging; and
discontinuing said process gas addition to the second medium when said desired second setpoint is reached, wherein the desired second setpoint is higher or lower than a redox potential of the second medium before said process gas addition.

18. The process of claim 4, wherein the first medium is selected from the group consisting of the unseeded composition after pasteurization, and the seeded composition before packaging and the unseeded composition before pasteurization has a redox potential lower than that of the first medium after said addition of process gas.

19. The process of claim 4, wherein the first medium is selected from the group consisting of the unseeded composition after pasteurization, and the seeded composition before packaging and the unseeded composition before pasteurization has a redox potential higher than that of the first medium after said addition of process gas.

* * * * *